United States Patent
Baker et al.

[11] Patent Number: 5,874,090
[45] Date of Patent: Feb. 23, 1999

[54] SUSTAINED-RELEASE FORMULATION OF METHYLPHENIDATE

[75] Inventors: Helen Frances Baker; Julian Clive Gilbert, both of Cambridge, United Kingdom

[73] Assignee: Medeva Europe Limited, London, United Kingdom

[21] Appl. No.: 679,875

[22] Filed: Jul. 15, 1996

[30] Foreign Application Priority Data

Jul. 14, 1995 [GB] United Kingdom ............... 9514451

[51] Int. Cl.[6] .................................... A61K 9/00
[52] U.S. Cl. .................. 424/400; 424/468; 424/489; 424/441; 424/470
[58] Field of Search ................... 424/400, 489, 424/468, 457

[56] References Cited

U.S. PATENT DOCUMENTS

| | | |
|---|---|---|
| 2,507,631 | 5/1950 | Hartmann et al. ............ 260/294 |
| 2,838,519 | 6/1958 | Rometsch . |
| 2,957,880 | 10/1960 | Rometsch . |
| 4,192,827 | 3/1980 | Mueller et al. ............ 525/122 |
| 5,583,140 | 12/1996 | Bencherif et al. ............ 514/299 |

OTHER PUBLICATIONS

Patrick, K. S. et al. (1987) "Pharmacology of the Enantiomers of threo–Methylphenidate" The Journal of Pharmacology and Experimental Therapeutics 241(1):152–158.

Eckerman, D.A. et al. (1991) "Enantioselective Behavioral Effects of threo–Methylphenidate in Rats" Pharmacology Biochemistry & Behavior 40:875–880.

*Primary Examiner*—Joseph L. Schofer
*Assistant Examiner*—William E. Benston, Jr.
*Attorney, Agent, or Firm*—Saliwanchik, Lloyd & Saliwanchik

[57] ABSTRACT

The subject invention pertains to a sustained-release formulation of d-threo-methylphenidate (dtmp). The subject invention also pertains to methods for treating disorders using a sustained-release formulation comprising d-threo-methylphenidate.

16 Claims, 1 Drawing Sheet

SUSTAINED-RELEASE FORMULATION OF METHYLPHENIDATE

FIELD OF THE INVENTION

This invention relates to a sustained-release formulation of methylphenidate.

BACKGROUND OF THE INVENTION

Methylphenidate is a known drug. It is used primarily to treat hyperactive children. It is a controlled substance.

Methylphenidate is a chiral molecule. The properties of the enantiomers have been investigated to some extent, although the drug is still administered as the racemate. It is generally thought that d-threo-methylphenidate (abbreviated herein as dtmp) is the active material, and that its antipode (ltmp) is metabolised more rapidly.

Methylphenidate is often administered in a sustained-release formulation. For example, a coated tablet comprising racemic methylphenidate is administered, with a view to maintaining a therapeutically-effective level of the drug in circulation. This formulation does not provide satisfactory or reproducible dosing.

Srinivas et al, Pharmaceutical Research 10(1):14 (1993), disclose a further disadvantage of known methylphenidate sustained-release formulations, i.e. that serum levels of the drug are increased by chewing. Many children chew tablets, and are therefore liable to receive an unnecessarily high dose of a controlled substance.

Patrick et al, Biopharmaceutics and Drug Disposition 10:165–171 (1989), describe the absorption of sustained-release methylphenidate formulations compared to an immediate-release formulation. It is suggested that the optimum dosage of methylphenidate for children is 0.5–0.7 mg/kg/day.

SUMMARY OF THE INVENTION

The present invention is based on an appreciation of the fact that, although it is possible to provide a model of chiral drug distribution, and measure the concentration of individual enantiomers and their breakdown products in a subject, over time, this is a poor model for understanding the effectiveness of the enantiomers. Since, after an initial period, the sustained-release formulation should ideally release the active material as evenly as possible, the administration of a racemate, i.e. of two related compounds, takes no account of interaction between the enantiomers. According to this invention, it has surprisingly been found both that there is considerable interaction, and that dtmp provides relatively linear kinetics within the clinically effective dose range in a suitable model, and is therefore suitable for incorporation in a sustained-release formulation. The experiments and data on which this discovery is based are given below.

DESCRIPTION OF THE INVENTION

Figure 1:
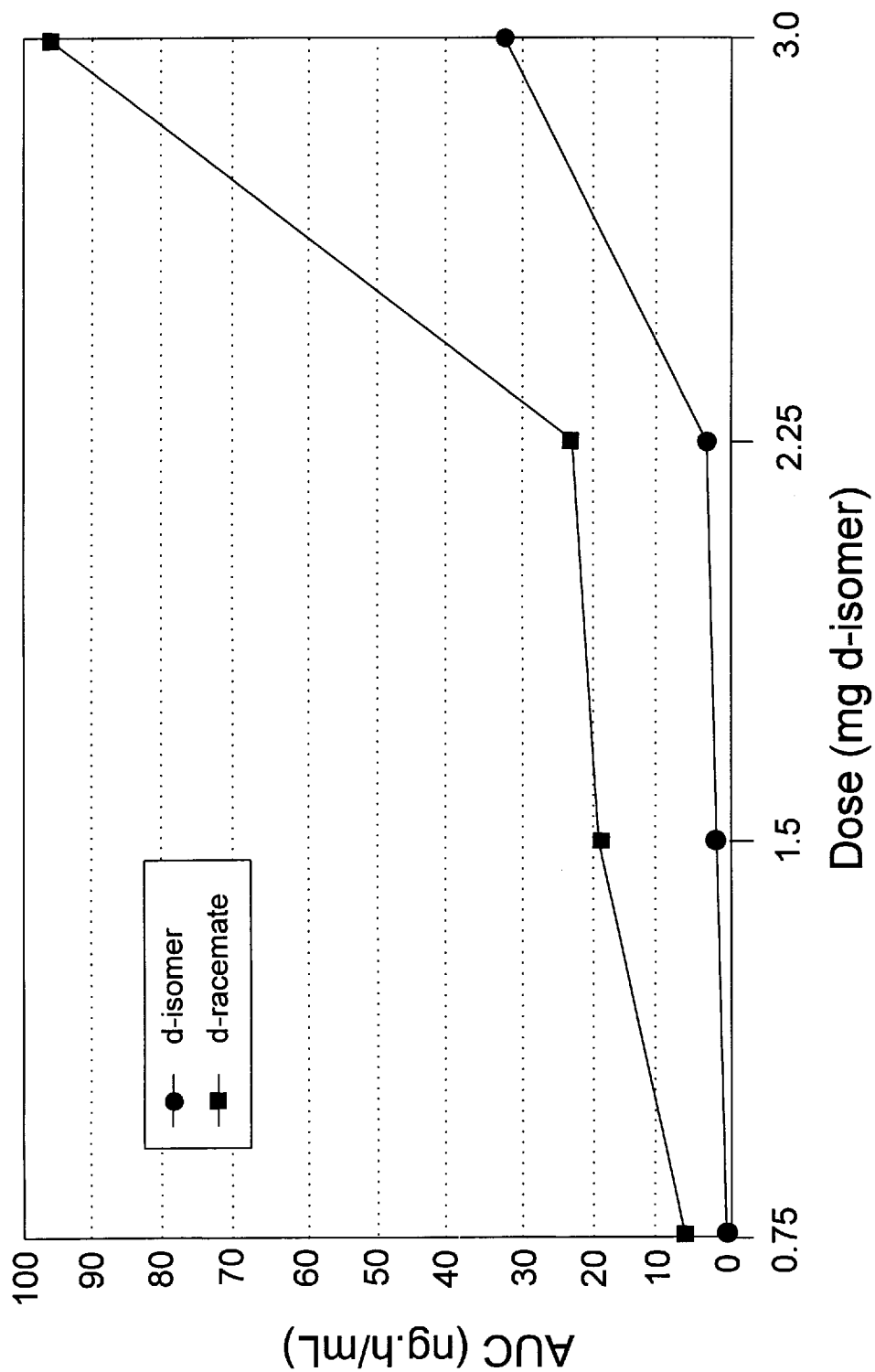
FIG. 1 shows a comparison of the area under the curve (AUC; ng.h/ml) for d-threo-methylphenidate (dtmp) and racemic methylphenidate at a range of doses.

The dtmp that is used in this invention is substantially free of its antipode (ltmp), e.g. in an enantiomeric excess (ee) of at least 70%, preferably at least 90%, and more preferably at least 95%. The dtmp may be substantially enantiopure. It may be used in the form of any suitable salt, e.g. the hydrochloride.

The dtmp may be administered by the same means as is known for racemic methylphenidate, in a sustained-release formulation, e.g. a coated tablet. It may be administered in any other conventional sustained-release formulation, via any suitable route of administration. Conventional dosing parameters may be adopted, i.e. those which are known to or adapted to the practice of those skilled in the art.

Compositions of the invention may be administered for known purposes, e.g. the treatment of attention-deficient hyperactivity disorder (ADHD; this term is used herein to encompass attention-deficit disorder) in pre-pubertal children and in adults, as a stimulant in cancer patients treated with narcotic analgesics, and also for the treatment of depression (e.g. in AIDS patients), compulsive shopping disorder, narcolepsy and hypersomnia. By contrast to known formulations of methylphenidate, the present invention may have any or all of the following advantages: linear kinetics within the clinically effective dose range, the reduction of exposure to a controlled substance, reduced side-effects (which include anorexia, insomnia, stomach ache and headache), reduced abuse potential, reduced $C_{max}$, a reduced level of active material even when chewed, reduced patient variability, reduced interaction with ltmp or other drugs, and less variability between fed and fasted subjects.

By controlling the nature of the formulation, it is possible to control dissolution in vitro, and thus match or exceed the U.S. National Formulary (NF) drug release profile for methylphenidate hydrochloride. Further, when administered to a healthy subject, a serum level of dtmp can be attained that is at least 50% of $C_{max}$, over a period of at least 8 hours, e.g. 8–16, 8–12 or 8–10 hours. Thus, for example, a shorter release period may be preferred or a different period before the serum level drops below a different proportion of $C_{max}$.

The serum level may be also controlled so that it remains high during the day, after taking a dosage in the morning, and is reduced in the evening, before it can have any undesirable effect on sleeping patterns. Preferably, the serum level is at least 50% $C_{max}$ after 8 hours and less than 25% $C_{max}$ after 12 to 16 hours.

A formulation of the invention may be a unit dosage such as a tablet, capsule or suspension. It may be in matrix, coating, reservoir, osmotic, ion-exchange or density exchange form. It may comprise a soluble polymer coating which is dissolved or eroded, after administration. Alternatively, there may be an insoluble coating, e.g. of a polymer, through which the active ingredient permeates, as from a reservoir, diffuses, e.g. through a porous matrix, or undergoes osmotic exchange. A further option for a sustained-release formulation involves density exchange, e.g. in the case where the formulation alters on administration, e.g. from microparticles to a gel, so that the active ingredient diffuses or permeates out. Ion-based resins may also be used, the active component being released by ionic exchange, and wherein the rate of release can be controlled by using cationic or anionic forms of the drug.

It is preferred to use a formulation in this invention that is resistant to chewing, e.g. micronised particles that are individually coated and which do not immediately release the active component on chewing, or possibly even actively discourage chewing by their consistency. The various effects etc may be due to the use of dtmp and/or the absence of ltmp.

Comparative Pharmacodynamics of d-threo-methylphenidate and Racemate

The study design was based on that described by Aoyama et al, J. Pharmacobio-Dyn. 13:647–652 (1990). Male Wistar rats were dosed with methylphenidate hydrochloride or its d-isomer at nominal dose levels of racemate: 1.5, 3, 4.5 or 6 mg base/kg body weight d-isomer: 0.75, 1.5, 2.25 or 3 mg base/kg body weight Blood samples were taken pre-dose, and 7 min, 15 min, 30 min, 45 min, 1 h, 1.5 h, 2 h, 3 h, 4.5 h, 6 h, 8 h post-dose. The samples were centrifuged to separate the plasma. Plasma samples were assayed for dtmp, by liquid chromatography mass spectrometry.

The results are shown in the accompanying drawing. FIG. 1 gives a comparison of the AUC (area under the curve) for values, obtained from plasma concentration of dtmp, versus time, for dtmp and methylphenidate (at equivalent dtmp quantities) dosed at a range of dtmp concentrations. Both curves show non-linear kinetics, evident as a point of disjunction in each curve. As the doses administered are increased, the quantity absorbed (i.e. AUC) increases in a linear fashion, until the disjunction, when the absorbed quantity is dramatically increased. This disjunction occurs within the clinically-relevant range (16–140 ng.h/ml in humans) for racemate dosing, but, surprisingly, is outside of this range for dtmp dosing.

This means that conventional dosing of the racemate, which involves increasing amounts of the drug, cannot be satisfactorily controlled. The possibility exists that a dosage will be given that is unnecessarily high.

Administration of dtmp has a surprising beneficial effect, in that a relatively linear dtmp AUC level in serum (lower curve) is achieved within the clinically-relevant range. The point of disjunction occurs outside the clinically-relevant range and, therefore, the flux of drug into and out of the circulatory system is more controllable. This makes dtmp suitable for incorporation in a sustained release formulation.

We claim:

1. A method for treating a human subject having a disorder capable of treatment with methylphenidate, which comprises administering to said subject a sustained-release formulation comprising an effective amount of d-threo-methylphenidate, wherein said sustained-release formulation is substantially free of 1-threo-methylphenidate.

2. The method according to claim 1, wherein at least the initial dosage is less than 15 mg d-threo-methylphenidate per day.

3. The method according to claim 1, wherein the disorder is attention-deficit hyperactivity disorder.

4. The method according to claim 1, wherein the amount of d-threo-methylphenidate administered is less than 1 mg/kg/day.

5. The method according to claim 1, wherein the amount of d-threo-methylphenidate administered is less than 0.5 mg/kg/day.

6. The method according to claim 1, which comprises administering a formulation comprising less than 20 mg d-threo-methylphenidate per unit dosage.

7. The method according to claim 6, which comprises administering a formulation comprising less than 15 mg d-threo-methylphenidate per unit dosage.

8. The method according to claim 1, wherein said sustained-release formulation is selected. from those comprising a soluble, erodible or otherwise modified coating, and those having an insoluble coating through which the d-threo-methylphenidate passes, in use.

9. The method according to claim 1, wherein said sustained-release formulation comprises d-threo-methylphenidate which is micronised.

10. The method according to claim 1, wherein said sustained-release formulation when administered to healthy subjects, provides a serum level of d-threo-methylphenidate of at least 50% $C_{max}$, over a period of at least 8 hours.

11. The method according to claim 10, wherein the period is 8 to 12 hours.

12. The method according to claim 10, wherein the serum level is less than 25% $C_{max}$ after 12 to 16 hours.

13. The method according to claim 1, wherein said sustained-release formulation upon administration to a healthy subject, provides $C_{max}$ of 2 to 20 ng/ml at a dosage of at least 2 mg.

14. The method according to claim 10, which on administration to a healthy subject, provides $C_{max}$ of 2 to 20 ng/ml at a dosage of at least 2 mg.

15. The method according to claim 10, wherein $C_{max}$ is substantially unaffected by chewing.

16. A method for treating a human subject having a disorder capable of treatment with methylphenidate, which comprises administering to said subject a sustained-release formulation comprising an effective amount of d-threo-methylphenidate, wherein said sustained-release formulation is substantially free of 1-threo-methylphenidate, and wherein said effective amount of d-threo-methylphenidate administered to said subject is about 16 to 140 ng.h/ml.

* * * * *